United States Patent
Nozawa et al.

(10) Patent No.: US 11,786,472 B2
(45) Date of Patent: Oct. 17, 2023

(54) PREPARATION CONTAINING SAXAGLIPTIN AND METHOD FOR PRODUCING THE SAME

(71) Applicant: SAWAI PHARMACEUTICAL Co., Ltd., Osaka (JP)

(72) Inventors: Kenji Nozawa, Osaka (JP); Wataru Izui, Osaka (JP); Ayane Natsume, Osaka (JP); Daiki Birukawa, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 17/354,167

(22) Filed: Jun. 22, 2021

(65) Prior Publication Data

US 2021/0393532 A1    Dec. 23, 2021

(30) Foreign Application Priority Data

Jun. 23, 2020  (JP) ................. 2020-107612

(51) Int. Cl.
 *A61K 9/20* (2006.01)
 *A61K 31/403* (2006.01)

(52) U.S. Cl.
CPC .......... *A61K 9/2086* (2013.01); *A61K 9/2009* (2013.01); *A61K 9/2018* (2013.01); *A61K 9/2054* (2013.01); *A61K 9/2059* (2013.01); *A61K 31/403* (2013.01)

(58) Field of Classification Search
None
See application file for complete search history.

(56) References Cited

U.S. PATENT DOCUMENTS

| | | | |
|---|---|---|---|
| 2005/0266080 A1 | 12/2005 | Desai et al. | |
| 2013/0224296 A1 | 8/2013 | Narang et al. | |
| 2014/0072628 A1* | 3/2014 | Kaushik | A61K 9/2886 514/412 |
| 2015/0250734 A1* | 9/2015 | Jain | A61K 9/2866 514/412 |

FOREIGN PATENT DOCUMENTS

| | | |
|---|---|---|
| JP | 4901727 B2 | 3/2012 |
| JP | 5837072 B2 | 12/2015 |

OTHER PUBLICATIONS

"Pharmaceutical Interview Form: Onglyza® tablets 2.5mg, 5mg." Revised on Aug. 2018 (9th edition), Kyowa Kirin Co., Ltd., Pharmaceutical, along with a partial English translation, cited in the Specification.

* cited by examiner

*Primary Examiner* — Susan T Tran
(74) *Attorney, Agent, or Firm* — Hauptman Ham, LLP

(57) ABSTRACT

A preparation containing saxagliptin having improved stability and a method for producing the same are provided. According to an embodiment of the present invention, a preparation containing saxagliptin including a plain tablet part containing one or more first additive agent selected from a group consisting of D-mannitol, lactose, anhydrous lactose, and anhydrous dibasic calcium phosphate, the plain tablet part containing less than 35% by weight of crystalline cellulose with respect to 100% by weight of the plain tablet part, and a film coating part in contact with the plain tablet part and containing saxagliptin, a salt thereof, or a hydrate thereof, and a method for producing the same are provided.

18 Claims, 5 Drawing Sheets

FIG. 2

| Component | Grade / Features | Example 1 | Example 2 | Example 3 | Example 4 | Comparative Example 1 |
|---|---|---|---|---|---|---|
| Lactose hydrate | Dilactose S | - | - | - | - | - |
| Anhydrous lactose | DCL-24 | - | 198 | - | - | - |
| D-mannitol | Granutol S | 198 | - | - | - | - |
| Anhydrous dibasic calcium phosphate | Fujicalin | - | - | - | 198 | - |
| Crystalline cellulose | PH102 | - | - | 198 | - | 198 |
| St-Mg | plant | 2 | 2 | 2 | 2 | 2 |
| Saxagliptin hydrate | - | 2.64 | 2.64 | 2.64 | 2.64 | 2.64 |
| PVA | EG-03P | 8 | 8 | 8 | 8 | 8 |
| PEG | 6000 | 4 | 4 | 4 | 4 | 4 |
| Talc | FUJI talc | 3 | 3 | 3 | 3 | 3 |
| Titanium oxide | NA-61 | 5 | 5 | 5 | 5 | 5 |
| HCl aq. | - | (200) | (200) | (200) | (200) | (200) |
| 25°C75%RH_1M | iminopiperazine ring (%) | 0.32 | 0.09 | 0.14 | 0.11 | 0.65 |

FIG. 3

| Component | Grade / Features | Example 1 | Example 5 | Example 6 | Example 7 | Example 8 | Example 9 | Example 10 | Comparative Example 2 |
|---|---|---|---|---|---|---|---|---|---|
| D-mannitol | Granutol S | 198 | 188 | 188 | 188 | 188 | 188 | 188 | 188 |
| Sodium starch glycolate | Primojel | - | - | - | - | - | - | - | 10 |
| Partially pregelatinized starch | PC-10 | - | - | 10 | - | - | - | - | - |
| Crospovidone | CL-F | - | - | - | 10 | - | - | - | - |
| Low-substituted hydroxypropyl cellulose | NBD-022 | - | 10 | - | - | - | - | - | - |
| Carmellose | NS300 | - | - | - | - | 10 | - | - | - |
| Carmellose calcium | ECG505 | - | - | - | - | - | 10 | - | - |
| Corn starch | XX16W | - | - | - | - | - | - | 10 | - |
| St-Mg | plant | 2 | 2 | 2 | 2 | 2 | 2 | 2 | 2 |
| Saxagliptin hydrate | - | 2.64 | 2.64 | 2.64 | 2.64 | 2.64 | 2.64 | 2.64 | 2.64 |
| PVA | EG-03P | 8 | 8 | 8 | 8 | 8 | 8 | 8 | 8 |
| PEG | 6000 | 4 | 4 | 4 | 4 | 4 | 4 | 4 | 4 |
| Talc | FUJI talc | 3 | 3 | 3 | 3 | 3 | 3 | 3 | 3 |
| Titanium oxide | NA-61 | 5 | 5 | 5 | 5 | 5 | 5 | 5 | 5 |
| HCl aq. | - | (200) | (200) | (200) | (200) | (200) | (200) | (200) | (200) |
| 25°C75%RH_1M | iminopiperazine ring (%) | 0.32 | 0.18 | 0.21 | 0.31 | 0.02 | 0.04 | 0.18 | 0.92 |

FIG. 4

| Component | Grade / Features | 1 | 11 | 12 | 13 | 14 | 15 | 16 | 17 | 18 | 19 | 20 | 21 | 22 | 23 | 24 | Comparative Example 3 |
|---|---|---|---|---|---|---|---|---|---|---|---|---|---|---|---|---|---|
| | | | | | | | | Example | | | | | | | | | |
| D-mannitol | GranuloIS | 198 | 193 | 188 | 183 | 178 | 168 | 158 | 148 | 138 | 118 | 168 | 158 | 148 | 138 | 128 | 36 |
| Crystalline cellulose | PH102 | - | - | - | - | - | - | - | - | - | - | 20 | 30 | 40 | 50 | 60 | 80 |
| Croscarmellose sodium | Ac-Di-Sol | - | 5 | 10 | 15 | 20 | 30 | 40 | 50 | 60 | 80 | 10 | 10 | 10 | 10 | 10 | - |
| Partially pregelatinized starch | PC-10 | - | - | - | - | - | - | - | - | - | - | - | - | - | - | - | 80 |
| Crospovidone | CL-F | - | - | - | - | - | - | - | - | - | - | - | - | - | - | - | 2 |
| St-Mg | plant | 2 | 2 | 2 | 2 | 2 | 2 | 2 | 2 | 2 | 2 | 2 | 2 | 2 | 2 | 2 | 2 |
| Saxagliptin hydrate | - | 2.64 | 2.64 | 2.64 | 2.64 | 2.64 | 2.64 | 2.64 | 2.64 | 2.64 | 2.64 | 2.64 | 2.64 | 2.64 | 2.64 | 2.64 | 2.64 |
| PVA | EG-03P | 8 | 8 | 8 | 8 | 8 | 8 | 8 | 8 | 8 | 8 | 8 | 8 | 8 | 8 | 8 | 8 |
| PEG | 6000 | 4 | 4 | 4 | 4 | 4 | 4 | 4 | 4 | 4 | 4 | 4 | 4 | 4 | 4 | 4 | 4 |
| Talc | FUJI talc | 3 | 3 | 3 | 3 | 3 | 3 | 3 | 3 | 3 | 3 | 3 | 3 | 3 | 3 | 3 | 3 |
| Titanium oxide | NA-61 | 5 | 5 | 5 | 5 | 5 | 5 | 5 | 5 | 5 | 5 | 5 | 5 | 5 | 5 | 5 | 5 |
| HCl aq. | - | (200) | (200) | (200) | (200) | (200) | (200) | (200) | (200) | (200) | (200) | (200) | (200) | (200) | (200) | (200) | (200) |
| 25°C/75%RH_1M aminopiperazine ring (%) | | 0.32 | 0.04 | 0.03 | 0.04 | 0.04 | 0.05 | 0.10 | 0.13 | 0.16 | 0.17 | 0.05 | 0.09 | 0.15 | 0.18 | 0.21 | 0.57 |

FIG. 5

| Component | Grade/Features | Example | | | Comparative Example | | | | | | | | | | | |
|---|---|---|---|---|---|---|---|---|---|---|---|---|---|---|---|---|
| | | 2 | 25 | 4 | 5 | 6 | 7 | 8 | 9 | 10 | 11 | 12 | 13 | 14 | 15 |
| Lactose hydrate | Dilactose S | 198 | 188 | 99 | 109 | 93 | 99 | 99 | 119 | 89 | 89 | 89 | 89 | 94 | 94 |
| Crystalline cellulose | PH102 | - | - | 90 | 90 | 90 | 90 | - | 70 | 90 | 90 | 90 | 90 | 90 | 90 |
| | UF711 | - | - | - | - | - | - | 90 | - | - | - | - | - | - | - |
| Croscarmellose sodium | Ac-Di-Sol | - | 10 | 10 | - | 16 | - | 10 | 10 | 10 | 10 | 10 | 10 | 10 | 10 |
| Sodium starch glycolate | Primojel | - | - | - | - | - | 10 | - | - | - | - | - | - | - | - |
| Light anhydrous silicic acid | Adsolider 101 | - | - | - | - | - | - | - | - | - | - | - | - | - | 5 |
| | Adsolider 102 | - | - | - | - | - | - | - | - | - | - | - | - | 5 | - |
| Methacrylic acid copolymer LD | L100-55 | - | - | - | - | - | - | - | - | - | - | - | 10 | - | - |
| Aminoalkyl Methacrylate Copolymer E | EPO | - | - | - | - | - | - | - | - | - | - | 10 | - | - | - |
| Magnesium oxide | - | - | - | - | - | - | - | - | - | 10 | - | - | - | - | - |
| Precipitated Calcium Carbonate | - | - | - | - | - | - | - | - | - | - | 10 | - | - | - | - |
| St-Mg | plant | 2 | 2 | 1 | 1 | 1 | 1 | 1 | 1 | 1 | 1 | 1 | 1 | 1 | 1 |
| Saxagliptin hydrate | - | 2.64 | 2.64 | 2.64 | 2.64 | 2.64 | 2.64 | 2.64 | 2.64 | 2.64 | 2.64 | 2.64 | 2.64 | 2.64 | 2.64 |
| PVA | EG-03P | 8 | 8 | 8 | 8 | 8 | 8 | 8 | 8 | 8 | 8 | 8 | 8 | 8 | 8 |
| PEG | 6000 | 4 | 4 | 4 | 4 | 4 | 4 | 4 | 4 | 4 | 4 | 4 | 4 | 4 | 4 |
| Talc | FUJI talc | 3 | 3 | 3 | 3 | 3 | 3 | 3 | 3 | 3 | 3 | 3 | 3 | 3 | 3 |
| Titanium oxide | NA-61 | 5 | 5 | 5 | 5 | 5 | 5 | 5 | 5 | 5 | 5 | 5 | 5 | 5 | 5 |
| HCl aq | - | (200) | (200) | (200) | (200) | (200) | (200) | (200) | (200) | (200) | (200) | (200) | (200) | (200) | (200) |
| 25°C75%RH_1M | iminopiperazine ring (%) | 0.09 | 0.04 | 0.52 | 0.49 | 0.54 | 0.87 | 0.55 | 0.42 | 18.73 | 1.21 | 5.60 | 1.09 | 0.74 | 1.31 |

PREPARATION CONTAINING SAXAGLIPTIN AND METHOD FOR PRODUCING THE SAME

CROSS-REFERENCE TO RELATED APPLICATIONS

This application is based upon and claims the benefit of priority from the prior Japanese Patent Application No. 2020-107612, filed on Jun. 23, 2020, the entire contents of which are incorporated herein by reference.

FIELD

The present invention relates to a preparation containing saxagliptin and a method for producing the same.

BACKGROUND

Saxagliptin ((1S,3S,5S)-2-[(2S)-2-Amino-2-(3-hydroxytricyclo[3.3.1.1$^{3.7}$]dec-1-yl)acetyl]-2-azabicyclo[3.1.0]hexane-3-carbonitrile monohydrate) is a selective inhibitor of dipeptidyl peptidase 4 (DPP4), which is a degradative enzyme of glucagon-like peptide-1 (GLP-1). GLP-1 stimulates pancreatic β-cells to enhance insulin secretion. Saxagliptin is effective as a type 2 diabetes mellitus therapeutic agent because it promotes insulin secretion by inhibiting the degradation of GLP-1 and exerts a hypoglycemic effect. A type 2 diabetes mellitus therapeutic agent containing saxagliptin includes, for example, Onglyza (registered trademark) Tablet (Onglyza Tablet 2.5 mg Onglyza Tablet 5 mg Interview Form).

Saxagliptin is known to be an unstable compound that tends to be intramolecularly cyclized. The cyclization reaction of saxagliptin is known to be accelerated by the producing process of a tablet containing saxagliptin and by contact with commonly used excipients.

Japanese Patent No. 4901727 discloses a saxagliptin containing tablet containing a tablet core including microcrystalline cellulose and lactose monohydrate as fillers, croscarmellose sodium as a disintegrant, and magnesium stearate as a lubricant, an inner seal coating layer including polyvinyl alcohol (PVA)-based polymer, and a second coating layer arranged on the inner seal coating layer and containing saxagliptin and the PVA-based polymer. Japanese Patent No. 5837072 discloses a saxagliptin containing tablet containing a water-soluble antioxidant such as ascorbic acid or propyl gallate in the inner seal coating layer and the second coating layer.

SUMMARY

One of the objects of the present invention is to provide a preparation containing saxaglipin having improved stability and a method for producing the same.

According to an embodiment of the present invention, a preparation containing saxagliptin including a plain tablet part containing one or more first additive agent selected from a group consisting of D-mannitol, lactose, anhydrous lactose, and anhydrous dibasic calcium phosphate, the plain tablet part containing less than 35% by weight of crystalline cellulose with respect to 100% by weight of the plain tablet part, and a film coating part in contact with the plain tablet part and containing saxagliptin, a salt thereof, or a hydrate thereof, and a method for producing the same is provided.

The plain tablet part may further contain one or more second additive agent selected from a group consisting of partially pregelatinized starch, low-substituted hydroxypropyl cellulose, crospovidone, croscarmellose sodium, carmellose, carmellose calcium, and corn starch.

The second additive agent may be selected from a group consisting of croscarmellose sodium, carmellose, and carmellose calcium.

The plain tablet part may contain 59% by weight or more of the first additive agent with respect to 100% by weight of the plain tablet part.

The plain tablet part may contain 2.5% by weight or more of the second additive agent with respect to 100% by weight of the plain tablet part.

The plain tablet part may contain 40% by weight or less of the second additive agent with respect to 100% by weight of the plain tablet part.

The first additive agent may be the D-mannitol or lactose, the second additive agent may be the croscarmellose sodium, and the plain tablet part may contain 69% by weight or more of the first additive agent and the second additive agent with respect to 100% by weight of the plain tablet part.

The film coating part may contain 40% by weight or more of polyvinyl alcohol with respect to 100% by weight of the film coating part excluding the saxagliptin.

BRIEF DESCRIPTION OF DRAWINGS

FIG. 2 is a table showing the type and amount of the additive agent and the amount of iminopiperazine ring (%) contained in the Examples and Comparative Examples;

FIG. 3 is a table showing the type and amount of the additive agent and the amount of iminopiperazine ring (%) contained in the Examples and Comparative Examples;

FIG. 4 is a table showing the type and amount of the additive agent and the amount of iminopiperazine ring (%) contained in the Examples and Comparative Examples; and FIG. 5 is a table showing the type and amount of the additive agent and the amount of iminopiperazine ring (%) contained in the Examples and Comparative Examples.

DESCRIPTION OF EMBODIMENTS

Hereinafter, a preparation containing saxagliptin and a method for producing the same according to the present invention will be described in detail. However, the preparation containing saxagliptin and the method for producing the same of the present invention are not to be construed as being limited to the description contents of the embodiments and examples shown below.

As a result of the investigation by the present inventors, it was found that when a plain tablet part was directly coated with a film containing saxagliptin, the stability of saxagliptin in the film coating part in a preparation containing saxagliptin was improved by adding a specific additive agent to the plain tablet part. Japanese Patent No. 4901727 and Japanese Patent No. 5837072 do not disclose or suggest that the surface of the plain tablet part is directly coated with the film containing saxagliptin.

Saxagliptin of the present embodiment is preferably (1S, 3S,5S)-2-[(2S)-2-Amino-2-(3-hydroxytricyclo[3.3.1.1$^{3.7}$] dec-1-yl)acetyl]-2-azabicyclo[3.1.0]hexane-3-carbonitrile monohydrate. However, the present invention is not limited thereto, saxagliptin, a salt thereof, or a hydrate thereof may be used. The content of saxagliptin can be appropriately selected according to the expected therapeutic effect, and, for example, one tablet of a preparation containing saxagliptin includes 2.5 mg or more and 5 mg or less of saxagliptin.

Figure 1B:
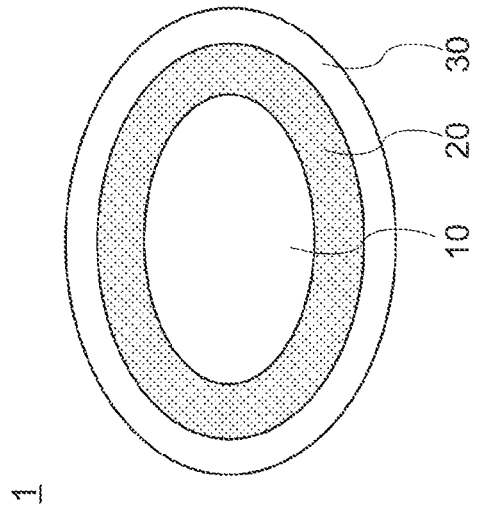
FIG. 1B is a cross-sectional view of a preparation containing saxagliptin according to the present embodiment.
Figure 1A:
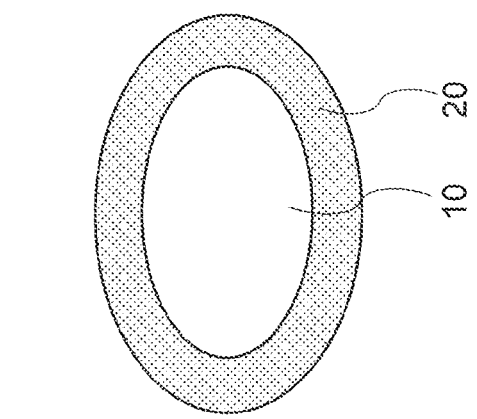
FIG. 1A is a cross-sectional view of a preparation containing saxagliptin according to the present embodiment.

As shown in FIG. 1A, a preparation 1 containing saxagliptin according to an embodiment of the present invention is a coated tablet containing a plain tablet part 10 and a film coating part 20 containing saxagliptin. The film coating part 20 is arranged so as to cover the surface of the plain tablet part 10. In the preparation 1 containing saxagliptin according to an embodiment of the present invention, it is sufficient that the plain tablet part 10 and the film coating part 20 containing saxagliptin are in contact with each other, and for example, a protective part 30 may be further included as shown in FIG. 1B. The protective part 30 is arranged so as to cover the surface of the film coating part 20.

The plain tablet part according to an embodiment contains, for example, one or more additive agents selected from the group consisting of D-mannitol, lactose, anhydrous lactose, and anhydrous dibasic calcium phosphate. The plain tablet part in the present embodiment preferably contains 59% by weight or more, preferably 65% by weight or more, and more preferably 84% by weight or more of one or more additive agents selected from the group consisting of D-mannitol, lactose, anhydrous lactose, and anhydrous dibasic calcium phosphate with respect to 100% by weight of the plain tablet part. Since the plain tablet part in the present embodiment contains 59% by weight or more of one or more additive agents selected from the group consisting of D-mannitol, lactose, anhydrous lactose, and anhydrous dibasic calcium phosphate with respect to 100% by weight of the plain tablet part, the generation of a related substance of saxagliptin upon storage can be suppressed and the stability of saxagliptin can be improved.

The plain tablet part according to an embodiment preferably does not contain crystalline cellulose. The content of crystalline cellulose in the plain tablet part in the present embodiment is preferably less than 35% by weight, more preferably 10% by weight or less with respect to 100% by weight of the plain tablet part.

The plain tablet part according to an embodiment may further contain croscarmellose sodium, partially pregelatinized starch, low-substituted hydroxypropyl cellulose, crospovidone, carmellose, carmellose calcium, or corn starch, and the like. An additive agent having a carboxymethyl cellulose structure such as croscarmellose sodium, carmellose, or carmellose calcium is particularly preferred because of its excellent stabilization of saxagliptin. It is more preferable that the plain tablet part in the present embodiment contains 2.5% by weight or more and 40% by weight or less of croscarmellose sodium, carmellose, or carmellose calcium with respect to 100% by weight of the plain tablet part. It is more preferable that the plain tablet part in the present embodiment contains 2.5% by weight or more and 15% by weight or less of croscarmellose sodium, carmellose, or carmellose calcium with respect to 100% by weight of the plain tablet part. Since the plain tablet part in the present embodiment contains croscarmellose sodium, carmellose, or carmellose calcium, the generation of a related substance of saxagliptin upon storage can be suppressed and the stability of saxagliptin can be improved.

The plain tablet part according to an embodiment preferably contains 69% by weight or more, and more preferably 90% by weight or more of D-mannitol and croscarmellose sodium, or lactose and croscarmellose sodium with respect to 100% by weight of the plain tablet part. Since the plain tablet part in the present embodiment contains 69% by weight or more of D-mannitol and croscarmellose sodium, or lactose and croscarmellose sodium with respect to 100% by weight of the plain tablet part, the generation of a related substance of saxagliptin upon storage can be suppressed and the stability of saxagliptin can be improved.

The plain tablet part according to an embodiment may further contain magnesium stearate or the like. The plain tablet part in the present embodiment preferably contains 0.5% by weight or more and 1% by weight or less of magnesium stearate with respect to 100% by weight of the plain tablet part.

The plain tablet part according to an embodiment is coated by the film coating part containing saxagliptin. The plain tablet part and the film coating part are in direct contact with each other.

The film coating part according to an embodiment contains saxagliptin. The film coating part according to an embodiment is preferably a polyvinyl alcohol-based film. The film coating part according to an embodiment preferably contains one or more additive agents selected from the group consisting of, for example, polyvinyl alcohol, polyethylene glycol, talc, and titanium oxide. The film coating part in the present embodiment may contain, for example, 40% by weight of polyvinyl alcohol, 20% by weight of polyethylene glycol, 15% by weight of talc, and 25% by weight of titanium oxide with respect to 100% by weight of the film coating part excluding saxagliptin.

The film coating part containing saxagliptin according to an embodiment may be further coated by the protective part. The film coating part and the protective part may be in direct contact with each other.

The protective part according to an embodiment may have the same composition as the film coating part other than containing no saxagliptin. The protective part may be a polyvinyl alcohol-based film. The protective part may contain one or more additive agents selected from the group consisting of, for example, polyvinyl alcohol, polyethylene glycol, talc, and titanium oxide. The protective part in the present embodiment may contain, for example, 40% by weight of polyvinyl alcohol, 20% by weight of polyethylene glycol, 15% by weight of talc, and 25% by weight of titanium oxide with respect to 100% by weight of the protective part.

In the preparation containing saxagliptin according to the present embodiment, by incorporating a specific additive agent into the plain tablet part, the generation of a related substance of saxagliptin upon storage can be suppressed and the stability of saxagliptin can be improved even if the plain tablet part is directly coated with the film containing saxagliptin.

The preparation containing saxagliptin according to the present embodiment can be produced according to a producing method known in the pharmaceutical field. In the method for producing the preparation containing saxagliptin according to the present embodiment, first, the additive agents selected from the above are homogeneously mixed, and the resulting mixture is tableted to produce the plain tablet part. At this time, other additive agents may be further added. The plain tablet part can be produced by compression molding with a commonly used tableting machine. For molding, any shape can be applied, for example, tablet, oval, spherical, or rod-shaped.

The resulting tablet part is then coated with the film containing saxagliptin to produce a preparation containing saxagliptin. Saxagliptin and the additive agent selected from the above are dissolved or dispersed in the solvent to prepare a coating liquid. At this time, other additive agents may be further added. The film coating part can be produced by directly spraying the resulting coating liquid onto the plain tablet part with a known coating apparatus to coat the plain tablet part and removing the solvent.

The resulting coated tablets may then be further coated with a saxagliptin-free film. The additive agents selected from the above are dissolved or dispersed in the solvent to prepare a coating liquid. At this time, other additive agents may be further added. The protective part can be produced by directly spraying the resulting coating liquid onto the film coating part with a known coating apparatus to coat the film coating part and removing the solvent.

In the method for producing the preparation containing saxagliptin according to the present embodiment, by incorporating a specific additive agent into the plain tablet part, the generation of a related substance of saxagliptin upon storage can be suppressed and the stability of saxagliptin can be improved even if the plain tablet part is directly coated with the film containing saxagliptin.

EXAMPLE

An example of a method for producing the preparation containing saxagliptin according to the present invention is shown below, but this description is merely an example and is not limited thereto.
(Producing of Preparation Containing Saxagliptin)

Additive agents were mixed, and the resulting mixture was tableted and molded by a rotary tableting machine (VELA5, KIKUSUI SEISAKUSHO LTD) to produce a plain tablet of 200 mg/tablet according to the Example and Comparative Example. Then, the coating liquid was prepared by dissolving or dispersing 2.64 mg of saxagliptin hydrate, 8 mg of polyvinyl alcohol, 4 mg of polyethylene glycol, 3 mg of talc, and 5 mg of titanium oxide per one tablet of each plain tablet in 200 g of hydrochloric acid, and by adjusting the pH to about 2 by adding sodium hydroxide. The preparation containing saxagliptin was obtained by spraying the coating liquid onto the surface of the plain tablet part using HC-LABO (Freund Corporation) to coat the tablet part and removing the solvent.
(Stability of Preparation Containing Saxagliptin)

The preparation containing saxagliptin was stored under the condition of 25° C., 75% RH for one month. As an assessment of stability, the purity of the preparation containing saxagliptin after storage was evaluated using a HPLC method. The sum of the peak areas of the components of saxagliptin and the related substance derived from saxagliptin obtained on a chromatogram was set to 100% by an area percentage method, and the amount of iminopiperazine ring (%), which was the main related substance derived from saxagliptin, was calculated from the ratio of the peak area. The type and amount (mg) of the additive agent and the amount of iminopiperazine ring (%) contained in each Example, Comparative Example are shown in FIGS. 2 to 5.

FIG. 2 shows the amount of iminopiperazine ring (%) derived from saxagliptin after storage in Examples 1 to 4 and Comparative Example 1. As shown in FIG. 2, Examples 1 to 4 containing 99% by weight of D-mannitol, lactose, anhydrous lactose, or anhydrous dibasic calcium phosphate with respect to 100% by weight of the plain tablet part showed a low amount of iminopiperazine ring (%). On the other hand, Comparative Example 1 containing 99% by weight of crystalline cellulose with respect to 100% by weight of the plain tablet part showed a high amount of iminopiperazine ring (%).

FIG. 3 shows the amount of iminopiperazine ring (%) derived from saxagliptin after storage in Examples 5 to 10 and Comparative Example 2. As shown in FIG. 3, Examples 5 to 10 containing 99% by weight of D-mannitol and low-substituted hydroxypropyl cellulose, D-mannitol and partially pregelatinized starch, D-mannitol and crospovidone, D-mannitol and carmellose, D-mannitol and carmellose calcium, or D-mannitol and corn starch with respect to 100% by weight of the plain tablet part showed a lower amount of iminopiperazine ring (%) compared to Example 1. On the other hand, Comparative Example 2 containing 99% by weight of D-mannitol and sodium starch glycolate with respect to 100% by weight of the plain tablet part showed a high amount of iminopiperazine ring (%).

FIG. 4 shows the amount of iminopiperazine ring (%) derived from saxagliptin after storage in Examples 11 to 24 and Comparative Example 3. As shown in FIG. 4, Examples 11 to 24 containing 59% by weight or more of D-mannitol with respect to 100% by weight of the plain tablet part showed a lower amount of iminopiperazine ring (%) compared to Example 1. Compared to Example 1, Examples 11 to 19 containing 99% by weight of D-mannitol and croscarmellose sodium with respect to 100% by weight of the plain tablet part showed an even lower amount of iminopiperazine ring (%). Compared to Example 1, Examples 11 to 19 containing 2.5% by weight to 40% by weight of croscarmellose sodium with respect to 100% by weight of the plain tablet part showed an even lower amount of iminopiperazine ring (%). Compared to Example 1, Examples 20 to 24 containing 10% by weight to 30% by weight of crystalline cellulose and 5% by weight of croscarmellose sodium with respect to 100% by weight of the plain tablet part showed a low amount of iminopiperazine ring (%). On the other hand, Comparative Example 3 containing 40% by weight of crystalline cellulose and 40% by weight of partially pregelatinized starch in the plain tablet part with respect to 100% by weight of the plain tablet part showed a high amount of iminopiperazine ring (%).

FIG. 5 shows the amount of iminopiperazine ring (%) derived from saxagliptin after storage in Example 25 and Comparative Examples 4 to 15.

As shown in FIG. 5, Example 25 containing 99% by weight of lactose and croscarmellose sodium with respect to 100% by weight of the plain tablet part showed a lower amount of iminopiperazine ring (%) compared to Example 2. Comparative Examples 4 to 15 containing 35% by weight or more of crystalline cellulose in the plain tablet part with respect to 100% by weight of the plain tablet part showed a higher amount of iminopiperazine ring (%) than in Example 2.

Even if it is other working effects which are different from the working effect brought about by the mode of each above-mentioned embodiment, what is clear from the description in this description, or what can be easily predicted by the person skilled in the art is naturally understood to be brought about by the present invention.

What is claimed is:
1. A preparation containing saxagliptin comprising:
a plain tablet part containing one or more first additive agent selected from a group consisting of D-mannitol, lactose, anhydrous lactose, and anhydrous dibasic calcium phosphate, the plain tablet part containing less than 35% by weight of crystalline cellulose with respect to 100% by weight of the plain tablet part; and
a film coating part in direct contact with the plain tablet part and containing saxagliptin, a salt thereof, or a hydrate thereof;

wherein the film coating part contains 40% by weight or more of polyvinyl alcohol with respect to 100% by weight of the film coating part excluding the saxagliptin.

2. The preparation containing saxagliptin according to claim 1, wherein;
the plain tablet part further contains one or more second additive agent selected from a group consisting of partially pregelatinized starch, low-substituted hydroxypropyl cellulose, crospovidone, croscarmellose sodium, carmellose, carmellose calcium, and corn starch.

3. The preparation containing saxagliptin according to claim 2, wherein;
the second additive agent is selected from a group consisting of croscarmellose sodium, carmellose, and carmellose calcium.

4. The preparation containing saxagliptin according to claim 1, wherein;
the plain tablet part contains 59% by weight or more of the first additive agent with respect to 100% by weight of the plain tablet part.

5. The preparation containing saxagliptin according to claim 2, wherein;
the plain tablet part contains 59% by weight or more of the first additive agent with respect to 100% by weight of the plain tablet part.

6. The preparation containing saxagliptin according to claim 3, wherein;
the plain tablet part contains 59% by weight or more of the first additive agent with respect to 100% by weight of the plain tablet part.

7. The preparation containing saxagliptin according to claim 2, wherein;
the plain tablet part contains 2.5% by weight or more of the second additive agent with respect to 100% by weight of the plain tablet part.

8. The preparation containing saxagliptin according to claim 3, wherein;
the plain tablet part contains 2.5% by weight or more of the second additive agent with respect to 100% by weight of the plain tablet part.

9. The preparation containing saxagliptin according to claim 7, wherein;
the plain tablet part contains 40% by weight or less of the second additive agent with respect to 100% by weight of the plain tablet part.

10. The preparation containing saxagliptin according to claim 8, wherein;
the plain tablet part contains 40% by weight or less of the second additive agent with respect to 100% by weight of the plain tablet part.

11. The preparation containing saxagliptin according to claim 3, wherein;
the first additive agent is the D-mannitol or lactose,
the second additive agent is the croscarmellose sodium, and
the plain tablet part contains 69% by weight or more of the first additive agent and the second additive agent with respect to 100% by weight of the plain tablet part.

12. A method for producing a preparation containing saxagliptin, comprising:
forming a plain tablet part by tableting a mixture containing one or more first additive agent selected from a group consisting of D-mannitol, lactose, anhydrous lactose, and anhydrous dibasic calcium phosphate, the mixture containing less than 35% by weight of crystalline cellulose with respect to 100% by weight of the plain tablet part; and
coating the plain tablet part with a film containing saxagliptin, a salt thereof, or a hydrate thereof directly onto the plain tablet part;
wherein the film coating part contains 40% by weight or more of polyvinyl alcohol with respect to 100% by weight of the film coating part excluding the saxagliptin.

13. The method according to claim 12, wherein;
the mixture further contains one or more second additive agent selected from a group consisting of partially pregelatinized starch, low-substituted hydroxypropyl cellulose, crospovidone, croscarmellose sodium, carmellose, carmellose calcium, and corn starch.

14. The method according to claim 13, wherein;
the second additive agent is selected from a group consisting of croscarmellose sodium, carmellose, and carmellose calcium.

15. The method according to claim 12, wherein;
the mixture contains 59% by weight or more of the first additive agent with respect to 100% by weight of the plain tablet part.

16. The method according to claim 13, wherein;
the mixture contains 2.5% by weight or more of the second additive agent with respect to 100% by weight of the plain tablet part.

17. The method according to claim 16, wherein;
the mixture contains 40% by weight or less of the second additive agent with respect to 100% by weight of the plain tablet part.

18. The method according to claim 14, wherein;
the first additive agent is the D-mannitol or lactose,
the second additive agent is the croscarmellose sodium, and
the mixture contains 69% by weight or more of the first additive agent and the second additive agent with respect to 100% by weight of the plain tablet part.

* * * * *